United States Patent
Goebbel et al.

(10) Patent No.: US 7,345,205 B2
(45) Date of Patent: Mar. 18, 2008

(54) METHOD FOR THE PRODUCTION OF TETRAHYDROGERANYLACETONE

(75) Inventors: Hans-Georg Goebbel, Kallstadt (DE); Gerd Kaibel, Lampertheim (DE); Christian Miller, Ruppertsberg (DE); Walter Dobler, Schwetzingen (DE); Thomas Dirnsteiner, Mainz (DE); Thilo Hahn, Ludwigshafen (DE); Klaus Breuer, Altrip (DE); Werner Aquila, Mannheim (DE)

(73) Assignee: BASF Aktiengesellschaft, Ludeigshafen (DE)

( * ) Notice: Subject to any disclaimer, the term of this patent is extended or adjusted under 35 U.S.C. 154(b) by 224 days.

(21) Appl. No.: 10/519,684

(22) PCT Filed: Jul. 14, 2003

(86) PCT No.: PCT/EP03/07600

§ 371 (c)(1),
(2), (4) Date: Jan. 10, 2005

(87) PCT Pub. No.: WO2004/007413

PCT Pub. Date: Jan. 22, 2004

(65) Prior Publication Data

US 2006/0211898 A1    Sep. 21, 2006

(30) Foreign Application Priority Data

Jul. 15, 2002    (DE) ................. 102 31 945

(51) Int. Cl.
*C07C 45/62*    (2006.01)

(52) U.S. Cl. ..................... 568/388; 568/398
(58) Field of Classification Search ............ None
See application file for complete search history.

(56) References Cited

U.S. PATENT DOCUMENTS

| 2,272,122 A |   | 2/1942 | Lee .................. 260/593 |
| 5,939,589 A | * | 8/1999 | Kaibel et al. ........ 568/568 |
| 6,150,564 A | * | 11/2000 | Brocker et al. ....... 568/462 |

FOREIGN PATENT DOCUMENTS

| DE | 226 872 | 9/1985 |
| EP | 0 798 039 | 10/1997 |
| EP | 0 947 493 | 10/1999 |
| GB | 788 301 | 12/1957 |

OTHER PUBLICATIONS

"Vitamins", Ullmann's Encyclopedia of Industrial Chemistry, 5$^{th}$ edition on CD-rom. chapter 4.11 1997.
Ullmanns Encyklopaedie der technischen Chemie, 4$^{th}$ edition, vol. 13, p. 138 1997.

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

A process is described for preparing tetrahydrogeranylacetone in which pseudoionone, geranylacetone and/or dihydrogeranylacetone in a liquid phase, in which particles of a catalyst which is capable of preferentially hydrogenating carbon-carbon double bonds over carbon-oxygen double bonds are suspended, is conducted through a device which inhibits the transport of the catalyst particles in the presence of a hydrogen-containing gas.

24 Claims, 2 Drawing Sheets

METHOD FOR THE PRODUCTION OF TETRAHYDROGERANYLACETONE

The present invention relates to a process for preparing tetrahydrogeranylacetone by selectively hydrogenating pseudoionone, geranylacetone and/or dihydrogeranylacetone.

Tetrahydrogeranylacetone (THGAC, hexahydropseudoionone) is used as a starting material for preparing isophytol which for its part is used as a reactant for preparing vitamin E and vitamin K (see, for example, Ullmann's Encyclopedia of Industrial Chemistry, 5th ed. on CD-Rom, "Vitamins", chapter 4.11).

GB 788,301 describes a process for preparing THGAC in which eranylacetone or dihydrogeranylacetone (tetrahydropseudoionone) is hydrogenated in the last step to THGAC.

In principle, THGAC should also be accessible by hydrogenating pseudoionone which may be prepared by reacting citral with acetone or by reacting dihydrolinalool with diketene or with isopropenyl methyl ether (see Ullmann's Encyclopedia of Industrial Chemistry, loc cit.). However, when preparing THGAC from pseudoionone, the problem occurs that three olefinic double bonds have to be selectively hydrogenated in the presence of a ketocarbonyl group (see scheme 1).

flow or fluidized bed reactors allow higher relative velocities, they require the use of distinctly larger catalyst particles so that the catalyst bed is more or less extensively expanded in the course of operation. However, the lower surface area relative to volume of relatively large catalyst particles limits the conversion and thus offsets the effect of the higher relative velocity.

U.S. Pat. No. 5,939,589 describes a process for carrying out catalytic reactions in which a liquid phase in which a catalyst is suspended and a gas phase in the reactor are conducted through a device which has orifices or channels having a hydraulic diameter of from 0.5 to 20 mm. The hydrogenation of hydrodehydrolinalool to hydrolinalool and further to tetrahydrolinalool is described. Hydrodehydrolinalool contains only one triple bond as a functional group to be hydrogenated, so those skilled in the art would not have discerned any suggestion with regard to selective hydrogenation.

It is an object of the present invention to provide a process for preparing THGAC from pseudoionone, geranylacetone and/or dihydrogeranylacetone which has a high selectivity with regard to the hydrogenation of C—C double bonds, i.e. in which the formation of 6,10-dimethylundecanol with reduction of the carbonyl group is substantially suppressed, and which combines the advantages of a high space-time yield and a simple catalyst exchange.

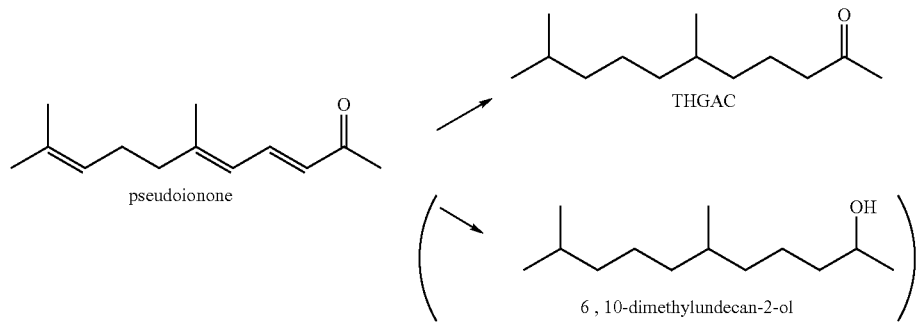

Scheme 1

Catalytic hydrogenations over heterogeneous catalysts are in many cases carried out using fixed bed reactors in order to obtain the advantages of continuous process operation. However, specially prepared catalysts have to be produced and used, and when they lose activity, often after only short onstream times, have to be exchanged or regenerated in a costly and inconvenient manner which generally involves not only the shutdown of the hydrogenation plant, but also of the subsequent workup stages.

Alternatively, a heterogeneously catalyzed hydrogenation may be carried out in the form of a suspension reaction by suspending the hydrogenation catalyst in a liquid phase with the introduction of mechanical energy, for example in a stirred tank, cf., for example, Ullmanns Encyklopadie der technischen Chemie, 4th ed., volume 13, 1997, p. 138, Verlag Chemie Weinheim. An increase in the energy introduced over and above the contribution necessary for suspension does not lead to a significant improvement in the mass transfer of the molecules to be hydrogenated to the surface of the catalyst particles, since the achievable relative velocity between the catalyst particles and the liquid phase only slightly exceeds the sedimentation velocity. Although

Figure 1:
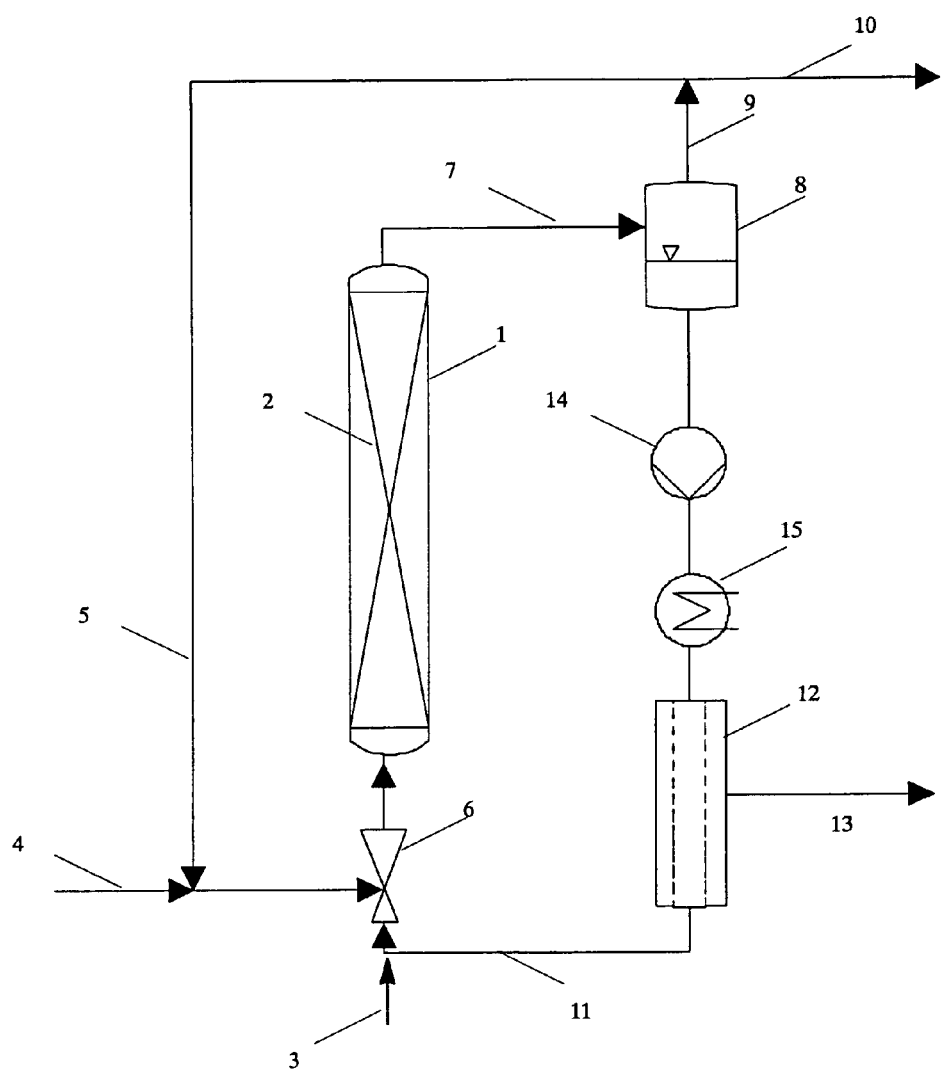
FIG. 1 shows a plant suitable for carrying out the process of the invention.

We have found that this object is achieved by a process in which pseudoionone, geranylacetone and/or dihydrogeranylacetone, preferably pseudoionone, in a liquid phase, in which particles of a catalyst which is capable of preferentially hydrogenating carbon-carbon double bonds over carbon-oxygen double bonds are suspended, is conducted through a device which inhibits the transport of the catalyst particles in the presence of a hydrogen-containing gas.

In the process according to the invention, a relatively high relative velocity of the liquid phase compared to the catalyst particles is obtained because the transport of the catalyst particles is inhibited by suitable means such as internals in a reactor, i.e. the particles are more strongly held back than the surrounding liquid. In combination with the high surface area relative to volume of the suspended particles, high space-time yields are achieved as a result.

A suitable device for carrying out the process according to the invention is described in EP-A 798 039.

The device inhibiting the transport of the catalyst particles preferably has orifices or channels whose hydraulic diameter is from 2 to 2000 times, in particular from 5 to 500 times, more preferably from 5 to 100 times, the average diameter of the catalyst particles.

The hydraulic diameter is a measure familiar to those skilled in the art for describing the equivalent diameter of noncircular channel structures. The hydraulic diameter of an orifice is defined as the quotient of 4 times the cross-sectional area of the orifice and its circumference. In the case of channels having a cross section in the shape of an isosceles triangle, the hydraulic diameter can be described as $$\frac{2bh}{b+2s}$$

where b is the base, h is the height and s is the congruent length of the triangle.

The orifices or channels of suitable devices generally have a hydraulic diameter of from 0.5 to 20 mm, preferably from 1 to 10 mm, more preferably from 1 to 3 mm.

Customarily, catalyst particles are used which have an average diameter of from 0.0001 to 2 mm, preferably from 0.001 to 1 mm, more preferably from 0.005 to 0.1 mm.

The device inhibiting the transport of the catalyst particles may comprise a dumped packing, a knit, an open-celled foam structure, preferably made of plastic, for example polyurethane or melamine resin, or ceramic, or a structured packing element, as already known in principle, i.e. by its geometric shape, from distillation and extracton technology. However, for the purposes of the present invention, structured packings in principle have a substantially smaller hydraulic diameter, frequently by a factor of from 2 to 10, than comparable internals in the field of distillation and extraction technology.

Useful structured packing elements are in particular metal fabric packings and wire fabric packings, for example of the design Montz A3, Sulzer BX, DX and EX. Instead of metal fabric packings, it is also possible to use structured packings made of other woven, knitted or felted materials. Further useful structured packings are of flat or corrugated sheets, preferably without perforation, or other relatively large orifices, for example corresponding to the designs Montz BI or Sulzer Mellapak. The structured packings made of expanded metal are also advantageous, for example structured packings of the type Montz BSH. A decisive factor for the suitability of the structured packing for the purposes of the present invention is not its geometry, but the orifice sizes and channel widths in the structured packing which are available for liquid flow.

In a preferred embodiment, the surfaces of the device facing toward the liquid phase have a roughness in the range from 0.1 to 10 times, preferably from 0.5 to 5 times, the average diameter of the catalyst particles. Preference is given to materials whose surfaces have an average roughness value $R_a$ (determined according to DIN 4768/1) of from 0.001 to 0.01 mm. When woven stainless steel wire packings are used, an appropriate surface roughness may be achieved by thermal treatment in the presence of oxygen, for example by heat treating the weave under air at a temperature of about 800° C.

The liquid phase preferably comprises at least 80% by weight, in particular at least 90% by weight, of pseudoionone, i.e. it preferably comprises no significant amounts of diluent. Although not preferred, the liquid phase may comprise diluents, for example $C_1$-$C_4$-alkanols, for example methanol.

The hydrogen-containing gas is generally hydrogen gas having a purity of at least 99.5% by volume. It is used in at least a stoichiometric quantity, based on the carbonyl compound present in the liquid phase, usually in an excess of from 1 to 20%.

The catalysts used may be a commercial suspension catalyst which is capable of preferentially hydrogenating carbon-carbon double bonds over carbon-oxygen double bonds. Particularly useful catalyts are those which comprise at least palladium as the active component. In addition to palladium, the catalyst may also comprise further active components, for example zinc, cadmium, platinum, silver or a rare earth metal such as cerium. The catalyst may be used in metallic and/or oxidic form. Preference is given to applying the active components to a support material. Examples of useful support materials include $SiO_2$, $TiO_2$, $ZrO_2$, $Al_2O_3$ or carbon such as graphite, carbon black or activated carbon. Owing to its easy suspendability, preference is given to activated carbon. The palladium content is preferably from 0.1 to 10% by weight, in particular from 0.5 to 7% by weight and more preferably from 2 to 6% by weight, based on the total weight of the catalyst.

The suspended catalyst material may be introduced into the liquid phase and is distributed within it with the aid of conventional techniques.

The device inhibiting the transport of the catalyst particles is customarily a plurality of internals in a reactor which are configured in such a manner that the reaction mixture is forced through the device when it passes through the reactor, i.e. the internals generally fill the entire free cross section of the reactor. The internals preferably, but not necessarily, extend over the entire elongation of the reactor in the flow direction of the liquid phase.

Various reactor forms are suitable, such as jet nozzle reactors, bubble columns or tube bundle reactors. Among these, a particularly suitable reactor is a vertical bubble column or a tube bundle reactor in which the internals are accommodated in the individual tubes.

Preference is given to conducting the hydrogen-containing gas and the liquid phase through the reactor in cocurrent, preferably against the direction of gravity. The gas phase is intimately mixed with the liquid phase, for example, by means of an injector nozzle. The superficial velocity of the liquid phase is preferably not more than 100 $m^3/m^2h$, in particular from 100 to 250 $m^3/m^2h$, and that of the gas phase is preferably more than 100 $m^3/m^2h$ (STP), in particular from 100 to 250 $m^3/m^2h$ (STP). In order to achieve sufficiently high superficial velocities, preference is given to recycling substreams of the gas and liquid phases which leave the reactor.

The catalyst particles suspended in the hydrogenation effluent are removed by customary processes, for example by sedimentation, centrifugation, cake filtration or crossflow filtration.

Preference is given to carrying out the process at a pressure of from 1 to 100 bar, more preferably from 1 to 50 bar, and in particular from 1 to 20 bar. The reaction temperature is preferably from 20 to 150° C., more preferably from 20 to 120° C. and in particular from 40 to 80° C.

The process according to the invention is illustrated by the appended figures and the example which follows.

FIG. 1 shows a schematic of a plant which is suitable for carrying out the process according to the invention and comprises a reactor (bubble column) 1 having a structured packing 2 which inhibits the transport of the catalyst particles. Liquid is introduced into the reactor via the line 3 and hydrogen gas via the line 4. The cycle gas 5 is mixed with fresh gas and the suspension 11 circulated by the pump 14 using the mixing nozzle 6. The reactor effluent is transferred via the line 7 into the separating vessel 8 in which the gas phase is separated and removed via line 9. A substream of this gas is withdrawn via line 10 to limit the accumulation of gaseous impurities and the remainder is conducted into the reactor via line 5. The suspended catalyst remains in the reactor system by being held back by a crossflow filter 12 and only catalyst-free liquid phase exits via line 13 and is withdrawn. The heat exchanger 15 can be used to precisely adjust the temperture in the reactor sytem.

Figure 2:
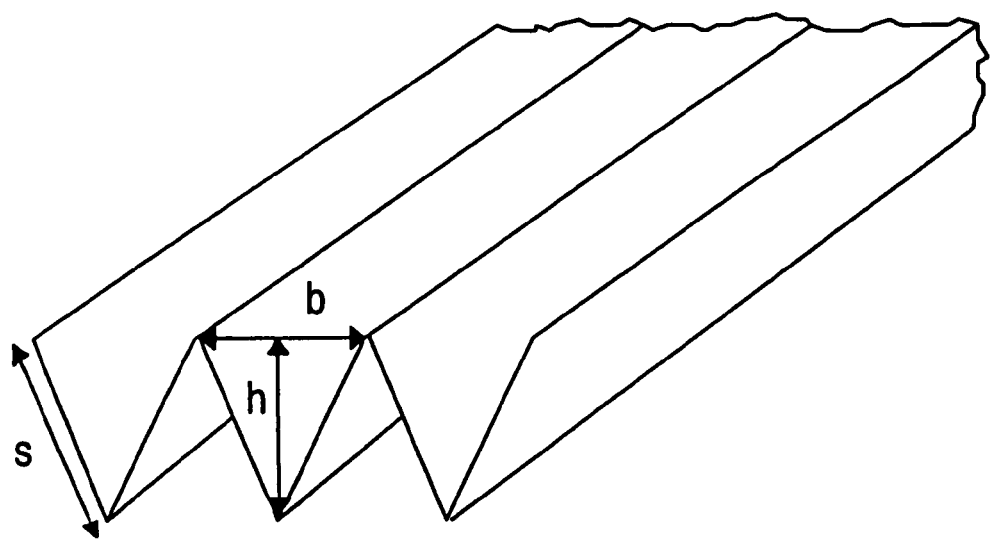
FIG. 2 shows a schematic of a layer of a corrugated weave.

FIG. 2 shows a schematic of a layer of a corrugated weave. Structured packings usable according to the invention are obtained when two or more of these layers are arranged on top of one another. Each layer comprises channels having a cross section in the shape of an isosceles triangle having the congruent length s, the base b and the height h.

EXAMPLES

A plant as described in FIG. 1 was used which comprised a bubble column (length 1000 mm, diameter 27.3 mm) equipped with a structured woven packing of the type Montz A3 1200. The structured packing consisted of layers arranged on top of one another of a stainless steel wire weave which was corrugated in such a way that channels having a cross section in the shape of an isosceles triangle were formed which had a congruent length 3.1 mm, base 5.1 mm and height 1.8 mm, corresponding to a hydraulic diameter of 1.62 mm.

Pseudoionone (97% by weight) with the catalyst suspended in it and hydrogen gas were introduced from below into the packed reactor in cocurrent at a superficial velocity of 200 $m^3/m^2*h$. The catalyst used was a commercial Pd-carbon suspension catalyst having a palladium content of 5% on activated carbon and an average particle size of 50 µm.

Example 1

The reaction was effected continuously under a hydrogen pressure of 10 bar and at a temperature of 100° C. A conversion of more than 99.9% was obtained and tetrahydrogeranylacetone was formed with a selectivity of more than 96%, based on the total amount of product. The selectivity for 6,10-dimethylundecan-2-ol was 3%. The catalyst hourly space velocity was 2-5 $kg_{pseudoionone}/(kg_{catalyst}*h)$; the space-time yield was 500 $kg_{pseudoionone}/(m^3*h)$.

Example 2

The reaction was effected continuously under a hydrogen pressure of 10 bar and at a temperature of 60° C. A conversion of more than 99.9% was obtained and tetrahydrogeranylacetone was formed with a selectivity of more than 96%, based on the total amount of product. The selectivity for 6,10-dimethylundecan-2-ol was 0.3%. The catalyst hourly space velocity was 2.5 $kg_{pseudoionone}/(kg_{catalyst}*h)$; the space-time yield was 500 $kg_{pseudoionone}/(m^3*h)$.

We claim:

1. A process for preparing tetrahydrogeranylacetone, comprising, passing a liquid phase, comprising at least 90% by weight of pseudoionone and in which particles of a catalyst which is capable of preferentially hydrogenating carbon-carbon double bonds over carbon-oxygen double bonds, and the active component of which comprises palladium are suspended, through a device which inhibits the transport of the catalyst particles in the presence of a hydrogen-containing gas.

2. A process as claimed in claim 1, wherein the device inhibiting the transport of the catalyst particles has orifices or channels whose hydraulic diameter is from 2 to 2000 times the average diameter of the catalyst particles.

3. A process as claimed in claim 1, wherein catalyst particles having an average diameter of from 0.0001 to 2 mm are used.

4. A process as claimed in claim 1, wherein the device used for inhibiting the transport of the catalyst particles is a dumped packing, a knit, an open-celled foam structure or a structured packing element.

5. A process as claimed in claim 1, wherein the liquid phase and the hydrogen-containing gas are conducted through the device which inhibits the transport of the catalyst particles at a superficial velocity of more than 100 $m^3/m^2h$.

6. A process as claimed in claim 1, wherein the surfaces of the device facing toward the liquid phase have a roughness in the range from 0.1 to 10 times the average diameter of the catalyst particles.

7. A process as claimed in claim 1, wherein the reaction pressure is from 1 to 100 bar.

8. A process as claimed in claim 1, wherein the reaction temperature is from 20 to 120° C.

9. A process for making tetrahydrogeranylacetone, comprising:
hydrogenating, in the liquid phase, the carbon-carbon double bonds of pseudoionone without hydrogenating the carbon-oxygen double bonds of the pseudoionone, wherein the hydrogenating is carried out by contacting a hydrogen-containing gas with a mixture comprising at least 90% by weight of pseudoionone,
wherein the mixture further comprises a catalyst having an active component comprising palladium, and
wherein during the hydrogenating the active component is suspended by a device that inhibits transport of particles of the catalyst.

10. The process as claimed in claim 9, wherein the device inhibiting the transport of particles of the catalyst has at least one of a plurality of orifices and a plurality of channels, wherein the orifices and the channels have a hydraulic diameter of from 2 to 2,000 times the average diameter of the particles of the catalyst.

11. The process as claimed in claim 9, wherein the particles of the catalyst have an average diameter of from 0.000 1 to 2 mm.

12. The process as claimed in claim 1, wherein the device used to inhibit transport of the particles of the catalyst is a dumped packing, a knit, an open-celled film structure or a structured packing element.

13. The process as claimed in claim 9, wherein the mixture phase and the hydrogen-containing gas are conducted through the device to inhibit transport of particles of the catalyst,
wherein the hydrogenating is carried out at a superficial velocity of more than 100 $m^3/m^2k$.

14. The process as claimed in claim 9, wherein the device has one or more surfaces contacting the mixture and having a roughness in the range of from 0.1 to 10 times the average diameter of the particles of the catalyst.

15. The process as claimed in claim 9, wherein a reaction pressure is from 1 to 100 bar.

16. The process as claimed in claim 9, wherein a reaction temperature is from 20 to 120° C.

17. The process as claimed in claim 1, wherein the liquid phase is essentially free of diluents.

18. The process as claimed in claim 1, wherein the liquid phase and the gas phase leaving the device are partially recycled to the device.

19. The process as claimed in claim 9, wherein the mixture comprises no diluents.

20. The process as claimed in claim 9, wherein a portion of the mixture and a portion of a gas phase leaving the device are partially recycled to the device.

21. The process as claimed in claim 1, wherein more than 96% of the psuedoionone is hydrogenated to selectively form tetrahydrogeranylacetone.

22. The process as claimed in claim 9, wherein more than 96% of the psuedoionone is hydrogenated to selectively form tetrahydrogeranylacetone.

23. The process as claimed in claim 21, wherein more than 99.9% of the psuedoionone is hydrogenated.

24. The process as claimed in claim 22, wherein more than 99.9% of the psuedoionone is hydrogenated.

* * * * *

UNITED STATES PATENT AND TRADEMARK OFFICE
CERTIFICATE OF CORRECTION

| | | |
|---|---|---|
| PATENT NO. | : 7,345,205 B2 | Page 1 of 1 |
| APPLICATION NO. | : 10/519684 | |
| DATED | : March 18, 2008 | |
| INVENTOR(S) | : Hans-Georg Goebbel et al. | |

It is certified that error appears in the above-identified patent and that said Letters Patent is hereby corrected as shown below:

On the title page, Item (73), the Assignee's city is spelled incorrectly. Item (73) should read:

-- (73) Assignee: BASF Aktiengesellschaft, Ludwigshafen (DE) --

Signed and Sealed this

Twenty-ninth Day of September, 2009

David J. Kappos
*Director of the United States Patent and Trademark Office*